United States Patent
Bardy et al.

(10) Patent No.: US 8,135,459 B2
(45) Date of Patent: *Mar. 13, 2012

(54) UNITARY SUBCUTANEOUS ONLY IMPLANTABLE CARDIOVERTER-DEFIBRILLATOR AND OPTIONAL PACER

(75) Inventors: Gust H. Bardy, Seattle, WA (US); Riccardo Cappato, Ferrara (IT)

(73) Assignee: Cameron Health, Inc., San Clemente, CA (US)

( * ) Notice: Subject to any disclaimer, the term of this patent is extended or adjusted under 35 U.S.C. 154(b) by 816 days.

This patent is subject to a terminal disclaimer.

(21) Appl. No.: 11/877,323

(22) Filed: Oct. 23, 2007

(65) Prior Publication Data

US 2008/0046014 A1    Feb. 21, 2008

Related U.S. Application Data

(60) Continuation of application No. 10/662,612, filed on Sep. 15, 2003, now Pat. No. 7,289,854, which is a division of application No. 09/663,606, filed on Sep. 18, 2000, now Pat. No. 6,647,292.

(51) Int. Cl.
*A61N 1/00* (2006.01)
(52) U.S. Cl. .......................................................... 607/4
(58) Field of Classification Search ................... 607/4–5, 607/9, 119
See application file for complete search history.

(56) References Cited

U.S. PATENT DOCUMENTS

| | | | |
|---|---|---|---|
| 3,986,496 A * | 10/1976 | Brastad .......................... 600/510 |
| 3,987,799 A * | 10/1976 | Purdy et al. ..................... 607/36 |
| 4,094,321 A * | 6/1978 | Muto .............................. 607/36 |
| 4,450,527 A | 5/1984 | Sramek |
| 4,567,900 A | 2/1986 | Moore |
| 4,603,705 A | 8/1986 | Speicher et al. |
| 4,693,253 A | 9/1987 | Adams |
| 4,719,920 A * | 1/1988 | Alt et al. .......................... 607/21 |
| 4,944,300 A | 7/1990 | Saksena |
| 5,105,810 A | 4/1992 | Collins et al. |
| 5,129,392 A | 7/1992 | Bardy et al. |
| 5,133,353 A | 7/1992 | Hauser |
| 5,170,784 A | 12/1992 | Ramon et al. |
| 5,203,348 A * | 4/1993 | Dahl et al. ..................... 607/129 |
| 5,255,692 A * | 10/1993 | Neubauer et al. ............. 607/122 |
| 5,261,400 A | 11/1993 | Bardy |
| 5,300,106 A * | 4/1994 | Dahl et al. ..................... 607/119 |
| 5,331,966 A * | 7/1994 | Bennett et al. ................ 600/508 |
| 5,342,407 A | 8/1994 | Dahl et al. |
| 5,388,578 A * | 2/1995 | Yomtov et al. ................ 600/375 |

(Continued)

OTHER PUBLICATIONS

Preliminary Amendment; filed Apr. 18, 2005; U.S. Appl. No. 10/949,877; Heinrich, et al.

(Continued)

*Primary Examiner* — Eric D Bertram
*Assistant Examiner* — Roland Dinga
(74) *Attorney, Agent, or Firm* — Pramudji Law Group PLLC; Ari Pramudji; Mark Schroeder

(57) ABSTRACT

A unitary subcutaneous implantable cardioverter-defibrillator which has a long thin housing in the shape of a patient's rib. The housing contains a source of electrical energy, a capacitor, and operational circuitry that senses the presence of potentially fatal heart rhythms. Provided on the housing are cardioversion/defibrillation electrodes located to deliver electrical cardioversion-defibrillation energy when the operational circuitry senses a potentially fatal heart rhythm. The unitary subcutaneous implantable cardioverter-defibrillator does not have a transvenous, intracardiac, epicardial, or subcutaneous electrode.

12 Claims, 3 Drawing Sheets

U.S. PATENT DOCUMENTS

| | | | |
|---|---|---|---|
| 5,405,363 | A | 4/1995 | Kroll et al. |
| 5,423,326 | A | 6/1995 | Wang et al. |
| 5,476,503 | A | 12/1995 | Yang |
| 5,534,022 | A | 7/1996 | Hoffmann et al. |
| 5,603,732 | A | 2/1997 | Dahl et al. |
| 5,618,287 | A * | 4/1997 | Fogarty et al. ............... 606/129 |
| 5,620,477 | A | 4/1997 | Pless et al. |
| 5,645,586 | A * | 7/1997 | Meltzer ................... 623/11.11 |
| 5,658,321 | A | 8/1997 | Fayram et al. |
| 5,776,169 | A * | 7/1998 | Schroeppel ................ 607/36 |
| 5,843,132 | A | 12/1998 | Ilvento |
| 5,895,414 | A * | 4/1999 | Sanchez-Zambrano ........ 607/36 |
| 5,957,956 | A | 9/1999 | Kroll et al. |
| 6,095,987 | A | 8/2000 | Shmulewitz et al. |
| 6,144,879 | A * | 11/2000 | Gray .......................... 607/20 |
| 6,266,567 | B1 | 7/2001 | Ishikawa et al. |
| 6,280,462 | B1 | 8/2001 | Hauser et al. |
| 6,522,915 | B1 * | 2/2003 | Ceballos et al. ............. 600/509 |
| 6,647,292 | B1 * | 11/2003 | Bardy et al. .................... 607/5 |
| 6,721,597 | B1 * | 4/2004 | Bardy et al. .................... 607/4 |
| 6,757,311 | B2 * | 6/2004 | Abe ......................... 372/43.01 |
| 7,720,534 | B2 * | 5/2010 | Bardy et al. .................... 607/2 |
| 7,720,536 | B2 * | 5/2010 | Rissmann et al. ............. 607/4 |
| 7,774,058 | B2 | 8/2010 | Ostroff et al. |
| 7,774,059 | B2 | 8/2010 | Ostroff et al. |
| 7,813,797 | B2 | 10/2010 | Bardy et al. |
| 7,835,790 | B2 | 11/2010 | Ostroff et al. |
| 2004/0215239 | A1 | 10/2004 | Favet |
| 2005/0021093 | A1 | 1/2005 | Brown |
| 2005/0038476 | A1 | 2/2005 | Brown |
| 2005/0107838 | A1 | 5/2005 | Lovett |
| 2005/0119707 | A1 | 6/2005 | Hauser |
| 2005/0131464 | A1 | 6/2005 | Heinrich |
| 2005/0143776 | A1 | 6/2005 | Brown |
| 2005/0277990 | A1 | 12/2005 | Ostroff et al. |
| 2006/0015163 | A1 | 1/2006 | Brown |
| 2006/0174898 | A1 | 8/2006 | Brown |
| 2007/0055314 | A1 | 3/2007 | Bardy et al. |
| 2007/0135847 | A1 | 6/2007 | Kenknight |
| 2007/0142865 | A1 | 6/2007 | Bardy et al. |
| 2008/0140139 | A1 | 6/2008 | Heinrich et al. |
| 2010/0228306 | A1 | 9/2010 | Bardy et al. |

OTHER PUBLICATIONS

Preliminary Amendment; filed Apr. 11, 2005; U.S. Appl. No. 10/968,889; Brown.

U.S. Appl. No. 60/252,811, filed Nov. 22, 2000; Heinrich, et al.

Response to Office Action; filed Jun. 28, 2007; U.S. Appl. No. 10/870,278; Brown.

U.S. Appl. No. 60/462,272, filed Apr. 11, 2003; Haefner, et al.

"Onset and Stability for Ventricular Tachyarrhythmia Detection in an Implantable Pacer-Cardioverter-Defibrillator"; IEEE Computes in Cardiology; 1987; vol. 0276-6574; pp. 167-170; by Walter H. Olsen, et al.

Office Action U.S. Appl. No. 09/663,606 (parent case); dated Oct. 15, 2002.

Response/Amendment (Feb. 22, 2011), Office Action (Aug. 23, 2010), Response/Amendment (Jun. 16, 2010), Restriction Requirement (Dec. 17, 2009), and Preliminary Amendment (Feb. 15, 2008); U.S. Appl. No. 11/981,410 (US 2008-0140139 A1—Heinrich, et al.).

Final Action (Jul. 13, 2010), Response/Amendment (Apr. 28, 2010), Interview Summary (Mar. 22, 2010), Restriction Requirement (Dec. 30, 2009), Response/Amendment (Oct. 19, 2009), Supplemental Office Action (Apr. 17, 2009), Interview Summaries (Apr. 14/16, 2009), Office Action (Oct. 17, 2008), Amendment/Response (Jun. 5, 2008), Interview Summary (May 28, 2008), Restriction Requirement (Dec. 6, 2007), and Preliminary Amendment (Apr. 11, 2005); U.S. Appl. No. 10/968,889 (US 2005-0143776 A1—Brown).

RCE, Amendment, and IDS (Feb. 1, 2011)Interview Summary (May 18, 2010, Final Action (Jan. 4, 2010), Response/Amendment (Oct. 19, 2009), Office Action (Apr. 20, 2009), Response/Amendment (Mar. 18, 2009), Interview Summary (Feb. 20, 2009), Restriction Requirement (Sep. 18, 2008), and Preliminary Amendment (Apr. 18, 2005); U.S. Appl. No. 10/949,877 (US 2005-0131464 A1—Heinrich, et al.).

RCE and Amendment (Jul. 16, 2010), Advisory Action (Jul. 2, 2010), Response/Amendment after Final (Jun. 16, 2010), Final Action (Apr. 16, 2010), Response/Amendment (Dec. 16, 2009), Office Action (Sep. 17, 2009), Response/Amendment (Jul. 2, 2009), and Restriction Requirement (Jun. 5, 2009); U.S. Appl. No. 11/680,107 (US 2007-0142865 A1—Bardy, et al.).

RCE and Amendment (Feb. 25, 2010), Advisory Action (Jan. 25, 2010), Response/Amendment after Final (Dec. 15, 2009), Final Action (Oct. 15, 2009), Response/Amendment (Jun. 19, 2009), and Office Action (Mar. 19, 2009); U.S. Appl. No. 11/554,185 (US 2007-0055314 A1—Bardy, et al.).

RCE, Amendment, and IDS (Feb. 28, 2011), Final Action (Nov. 26, 2010), Response/Amendment (Dec. 15, 2009), Office Action (Sep. 16, 2009), Response/Amendment after Final (Aug. 24, 2009), Final Action (Jun. 23, 2009), Response/Amendment (Mar. 23, 2009), Office Action (Dec. 24, 2008), Response/Amendment (Apr. 16, 2008), and Office Action (Jan. 16, 2008); U.S. Appl. No. 11/205,447 (US 2005-0277990 A1—Ostroff, et al.).

* cited by examiner

UNITARY SUBCUTANEOUS ONLY IMPLANTABLE CARDIOVERTER-DEFIBRILLATOR AND OPTIONAL PACER

RELATED APPLICATIONS

This application is a continuation of U.S. patent application Ser. No. 10/662,612, filed Sep. 15, 2003, now U.S. Pat. No. 7,289,854 and titled "Unitary Subcutaneous Only Implantable Cardioverter-Defibrillator and Optional Pacer"; which is a divisional of U.S. patent application Ser. No. 09/663,606, filed Sep. 18, 2000, now U.S. Pat. No. 6,647,292, and titled "Unitary Subcutaneous Only Implantable Cardioverter-Defibrillator and Optional Pacer"; the entire disclosures of which are incorporated herein by reference.

This application is related to commonly owned U.S. patent application Ser. No. 09/663,607, filed Sep. 18, 2000, now U.S. Pat. No. 6,721,597, and entitled "Subcutaneous Only Implantable Cardioverter-Defibrillator and Optional Pacer", the entire disclosure of which is incorporated herein by reference.

FIELD OF THE INVENTION

The present invention relates to an apparatus and method for performing electrical cardioversion/defibrillation and optional pacing of the heart via a totally subcutaneous non-transvenous system.

BACKGROUND OF THE INVENTION

Defibrillation/cardioversion is a technique employed to counter arrhythmic heart conditions including some tachycardias in the atria and/or ventricles. Typically, electrodes are employed to stimulate the heart with electrical impulses or shocks of a magnitude substantially greater than pulses used in cardiac pacing.

Defibrillation/cardioversion systems include body implantable electrodes and are referred to as implantable cardioverter/defibrillators (ICDs). Such electrodes can be in the form of patches applied directly to epicardial tissue, or at the distal end regions of intravascular catheters, inserted into a selected cardiac chamber. U.S. Pat. Nos. 4,603,705; 4,693,253; 4,944,300; and 5,105,810, the disclosures of which are all incorporated herein by reference, disclose intravascular or transvenous electrodes, employed either alone or in combination with an epicardial patch electrode. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat. No. 5,476,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of a pulse monitor/generator surgically implanted into the abdomen and subcutaneous electrodes implanted in the thorax. This system is far more complicated to use than current ICD systems using transvenous lead systems together with an active can electrode, and therefore it has no practical use. It has, in fact, never been used because of the surgical difficulty of applying such a device (3 incisions), the impractical abdominal location of the generator and the electrically poor sensing and defibrillation aspects of such a system.

Recent efforts to improve the efficiency of ICDs have led manufacturers to produce ICDs which are small enough to be implanted in the pectoral region. In addition, advances in circuit design have enabled the housing of the ICD to form a subcutaneous electrode. Some examples of ICDs in which the housing of the ICD serves as an optional additional electrode are described in U.S. Pat. Nos. 5,133,353; 5,261,400; 5,620,477; and 5,658,321, the disclosures of which are incorporated herein by reference.

ICDs are now an established therapy for the management of life-threatening cardiac rhythm disorders, primarily ventricular fibrillation (V-Fib). ICDs are very effective at treating V-Fib, but are therapies that still require significant surgery.

As ICD therapy becomes more prophylactic in nature and used in progressively less ill individuals, the requirement of ICD therapy to use intravenous catheters and transvenous leads is an impediment to very long-term management as most individuals will begin to develop complications related to lead system malfunction sometime in the 5-10 year time frame, often earlier. In addition, chronic transvenous lead systems, their implantation and removals, can damage major cardiovascular venous systems and the tricuspid valve, as well as result in life-threatening perforations of the great vessels and heart. Consequently, use of transvenous lead systems, despite their many advantages, are not without their chronic patient management limitations in those with life expectancies of >5 years. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of automatic external defibrillator (AED) therapy. AEDs employ the use of cutaneous patch electrodes to effect defibrillation under the direction of a bystander user who treats the patient suffering from V-Fib. AEDs can be as effective as an ICD if applied to the victim promptly within 2 to 3 minutes.

AED therapy has great appeal as a tool for diminishing the risk of death in public venues such as in air flight. However, an AED must be used by another individual, not the person suffering from the potentially fatal rhythm. It is more of a public health tool than a patient-specific tool like an ICD. Because >75% of cardiac arrests occur in the home, and over half occur in the bedroom, patients at risk of cardiac arrest are often alone or asleep and cannot be helped in time with an AED. Moreover, its success depends to a reasonable degree on an acceptable level of skill and calm by the bystander user.

What is needed, therefore, is a combination of the two forms of therapy which would provide prompt and near-certain defibrillation, like an ICD, but without the long-term adverse sequelae of a transvenous lead system while simultaneously using most of the simpler and lower cost technology of an AED. What is also needed is a cardioverter/defibrillator that is of simple design and can be comfortably implanted in a patient for many years. We call such a device a unitary subcutaneous only ICD (US-ICD) and is described in detail below.

SUMMARY OF THE INVENTION

The preferred embodiment for the unitary subcutaneous only ICD (US-ICD) with optional pacing consists of five basic components: 1) a curved housing which houses a battery supply, capacitor, and operational circuitry; 2) two cardioversion/defibrillating electrodes are attached to the outer surface of the housing; 3) one or more sensing electrodes located on the housing; and 4) sense circuitry suitable to an ICD or AED V-Fib detection algorithm. Additionally, an application system is provided for simple insertion of the US-ICD. No transvenous lead system is used, eliminating a significant impediment to broader scale prophylactic use.

The housing will provide energy and voltage intermediate to that available with ICDs and AEDs. The typical maximum voltage necessary for ICDs using most biphasic waveforms is approximately 750 V and associated maximum energy of approximately 40 J. The typical maximum voltage necessary for AEDs is approximately 2000-5000 V with an associated maximum energy of approximately 150-360 J. The US-ICD of the present invention will use voltages in the range of 800 to 2000 V and associated with energies of approximately 40-150 J.

The cardioversion/defibrillation electrodes are electrically insulated from each other and are about 5-10 cm in length. In the preferred embodiment, the sense electrodes are located between the cardioversion/defibrillation electrodes and are spaced about 4 cm from each other to provide a reasonable QRS signal from a subcutaneous extracardiac sampling location but may be of variable length to allow for sense optimization.

The sense circuitry in the preferred embodiment is designed to be highly sensitive and specific to the presence or absence of life-threatening ventricular arrhythmias only. Features of the detection algorithm are programmable, but the algorithm is focused on the detection of V-Fib and high rate ventricular tachycardia (V-Tach) of greater than 240 bpm. This type of cardioverter-defibrillator is not necessarily designed to replace ICD therapy for those with pre-identified problems of V-Tach/V-Fib or even atrial fibrillation, but is particularly geared to use as a prophylactic, long-term device, used for the life of the patient at risk of his/her first V-Fib/V-Tach event. The device of the present invention may infrequently be used for an actual life-threatening event but can be employed in large populations of individuals at modest risk and with modest cost by physicians of limited experience. Consequently, the preferred embodiment of the present invention focuses only on the detection and therapy of the most malignant rhythm disorders. As part of the detection algorithm's applicability to children, the upper rate range is programmable upward for use in children, who are known to have more rapid supraventricular tachycardias as well as more rapid ventricular tachycardias compared to adults.

The incision to apply the device of the present invention can be anywhere on the thorax although in the preferred embodiment, the device of the present invention will be applied in the anterior mid-clavicular line approximately at the level of the mammary crease beneath the left areolus. A subcutaneous path will then be made and will extend to the posterior thoracic region ideally at the level of the inferior scapula tip. Such a lead position will allow for a good transthoracic current delivery vector as well as positioning of the proximally positioned sense bipole in a good location for identification of the QRS ECG signal. A specially designed curved introducer set, through which local anesthetic can be delivered, is provided to assist in the placement of the US-ICD.

BRIEF DESCRIPTION OF THE DRAWINGS

For a better understanding of the invention, reference is now made to the drawings where like numerals represent similar objects throughout the figures where.

DESCRIPTION OF THE PREFERRED EMBODIMENTS

Figure 1:
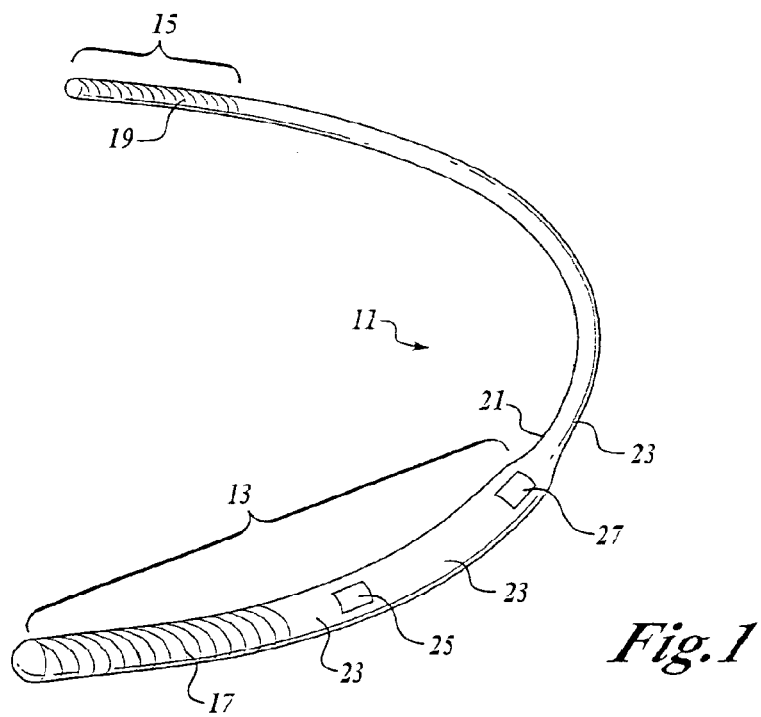
FIG. 1 is a schematic view of a Unitary Subcutaneous ICD (US-ICD) of the present invention.

Turning now to FIG. 1, the US-ICD of the present invention is illustrated. The US-ICD consists of a curved housing 11 with a first and second end. The first end 13 is thicker than the second end 15. This thicker area houses a battery supply, capacitor and operational circuitry for the US-ICD. The circuitry will be able to monitor cardiac rhythms for tachycardia and fibrillation, and if detected, will initiate charging the capacitor and then delivering cardioversion/defibrillation energy through the two cardioversion/defibrillating electrodes 17 and 19 located on the outer surface of the two ends of the housing. Examples of such circuitry are described in U.S. Pat. Nos. 4,693,253 and 5,105,810, the entire disclosures of which are incorporated herein by reference. The circuitry can provide cardioversion/defibrillation energy in different types of waveforms. In the preferred embodiment, a 100 uF biphasic waveform is used of approximately 10-20 ms total duration and with the initial phase containing approximately $\frac{2}{3}$ of the energy. However, any type of waveform can be utilized such as monophasic, biphasic, multiphasic or alternative waveforms as is known in the art.

In addition to providing cardioversion/defibrillation energy, the circuitry can also provide transthoracic cardiac pacing energy. The optional circuitry will be able to monitor the heart for bradycardia and/or tachycardia rhythms. Once a bradycardia or tachycardia rhythm is detected, the circuitry can then deliver appropriate pacing energy at appropriate intervals through the electrodes. Pacing stimuli will be biphasic in the preferred embodiment and similar in pulse amplitude to that used for conventional transthoracic pacing.

This same circuitry can also be used to deliver low amplitude shocks on the T-wave for induction of ventricular fibrillation for testing S-ICD performance in treating V-Fib as is described in U.S. Pat. No. 5,129,392, the entire disclosure of which is incorporated herein by reference. Also, the circuitry can be provided with rapid induction of ventricular fibrillation or ventricular tachycardia using rapid ventricular pacing. Another optional way for inducing ventricular fibrillation would be to provide a continuous low voltage, i.e., about 3 volts, across the heart during the entire cardiac cycle.

Another optional aspect of the present invention is that the operational circuitry can detect the presence of atrial fibrillation as described in Olson, W. et al., "Onset and Stability for Ventricular Tachyarrhythmia Detection in an Implantable Cardioverter and Defibrillator," *IEEE Computers in Cardiology*, (1986) pp. 167-170, the disclosure of which is incorporated herein by reference. Detection can be provided via R-R cycle length instability detection algorithms. Once atrial fibrillation has been detected, the operational circuitry will then provide QRS synchronized atrial defibrillation/cardioversion using the same shock energy and waveshape characteristics used for ventricular defibrillation/cardioversion.

The sensing circuitry will utilize the electronic signals generated from the heart and will primarily detect QRS waves. In one embodiment, the circuitry will be programmed to detect only ventricular tachycardias or fibrillations. The detection circuitry will utilize in its most direct form a rate detection algorithm that triggers charging of the capacitor once the ventricular rate exceeds some predetermined level for a fixed period of time, for example, if the ventricular rate exceeds 240 bpm on average for more than 4 seconds. Once the capacitor is charged, a confirmatory rhythm check would ensure that the rate persists for at least another 1 second before discharge. Similarly, termination algorithms could be instituted that ensure that a rhythm less than 240 bpm persisting for at least 4 seconds before the capacitor charge is drained to an internal resistor. Detection, confirmation and termination algorithms as are described above and in the art can be modulated to increase sensitivity and specificity by examining electrocardiographic QRS beat-to-beat uniformity, QRS signal frequency content, R-R interval stability data, and signal amplitude characteristics, all or part of which can be used to increase or decrease both sensitivity and specificity of US-ICD arrhythmia detection function.

In addition to use of the sense circuitry for detection of V-Fib or V-Tach by examining the QRS waves, the sense circuitry can check for the presence or the absence of respiration. The respiration rate can be detected by monitoring the impedance across the thorax using subthreshold currents delivered across the active can and the high voltage subcutaneous lead electrode and monitoring the frequency in undulation in the waveform that results from the undulations of transthoracic impedance during the respiratory cycle. If there is no undulation, then the patient is not respiring and this lack of respiration can be used to confirm the QRS findings of cardiac arrest. The same technique can be used to provide information about the respiratory rate or estimate cardiac output as described in U.S. Pat. Nos. 6,095,987; 5,423,326; and 4,450,527, the entire disclosures of which are incorporated herein by reference.

The housing of the present invention can be made out of titanium alloy or other presently preferred ICD designs. It is contemplated that the housing is also made out of biocompatible plastic materials that electronically insulate the electrodes from each other. However, it is contemplated that a malleable canister that can conform to the curvature of the patient's chest will be preferred. In this way, the patient can have a comfortable canister that conforms to the unique shape of the patient's rib cage. Examples of conforming ICD housings are provided in U.S. Pat. No. 5,645,586, the entire disclosure of which is incorporated herein by reference. In the preferred embodiment, the housing is curved in the shape of a $5^{th}$ rib of a person. Because there are many different sizes of people, the housing will come in different incremental sizes to allow a good match between the size of the rib cage and the size of the US-ICD. The length of the US-ICD will range from about 15 to about 50 cm. Because of the primary preventative role of the therapy and the need to reach energies over 40 Joules, a feature of the preferred embodiment is that the charge time for the therapy intentionally be relatively long to allow capacitor charging within the limitations of device size.

The thick end of the housing is currently needed to allow for the placement of the battery supply, operational circuitry, and capacitors. It is contemplated that the thick end will be about 0.5 cm to about 2 cm wide, with about 1 cm being presently preferred. As microtechnology advances, the thickness of the housing will become smaller. Examples of small ICD housings are disclosed in U.S. Pat. Nos. 5,957,956 and 5,405,363, the entire disclosures of which are incorporated herein by reference.

The two cardioversion/defibrillation electrodes on the housing are used for delivering the high voltage cardioversion/defibrillation energy across the heart. In the preferred embodiment, the cardioversion/defibrillation electrodes are coil electrodes. However, other cardioversion/defibrillation electrodes could be used such as having electrically isolated active surfaces or platinum alloy electrodes. The coil cardioversion/defibrillation electrodes are about 5-10 cm in length. Located on the housing between the two cardioversion/defibrillation electrodes are two sense electrodes 25 and 27. The sense electrodes are spaced far enough apart to be able to have good QRS detection. This spacing can range from 1 to 10 cm with 4 cm being presently preferred. The electrodes may or may not be circumferential with the preferred embodiment. Having the electrodes non-circumferential and positioned outward, toward the skin surface, is a means to minimize muscle artifact and enhance QRS signal quality. The sensing electrodes are electrically isolated from the cardioversion/defibrillation electrode via insulating areas 23. Analogous types of cardioversion/defibrillation electrodes are currently commercially available in a transvenous configuration. For example, U.S. Pat. No. 5,534,022, the entire disclosure of which is incorporated herein by reference, discloses a composite electrode with a coil cardioversion/defibrillation electrode and sense electrodes. Modifications to this arrangement are contemplated within the scope of the invention. One such modification is to have the sense electrodes at the two ends of the housing and have the cardioversion/defibrillation electrodes located in between the sense electrodes. Another modification is to have three or more sense electrodes spaced throughout the housing and allow for the selection of the two best sensing electrodes. If three or more sensing electrodes are used, then the ability to change which electrodes are used for sensing would be a programmable feature of the US-ICD to adapt to changes in the patient physiology and size over time. The programming could be done via the use of physical switches on the canister, or as presently preferred, via the use of a programming wand or via a wireless connection to program the circuitry within the canister.

The housing will provide energy and voltage intermediate to that available with ICDs and most AEDs. The typical maximum voltage necessary for ICDs using most biphasic waveforms is approximately 750 volts with an associated maximum energy of approximately 40. Joules. The typical maximum voltage necessary for AEDs is approximately 2000-5000 volts with an associated maximum energy of approximately 200-360 Joules depending upon the model and waveform used. The US-ICD of the present invention uses maximum voltages in the range of about 800 to about 2000 volts and is associated with energies of about 40 to about 150 Joules. The capacitance of the S-ICD could range from about 50 to about 200 micro farads.

The sense circuitry contained within the housing is highly sensitive and specific for the presence or absence of life-threatening ventricular arrhythmias. Features of the detection algorithm are programmable, and the algorithm is focused on the detection of V-Fib and high rate V-Tach (>240 bpm). Although the US-ICD of the present invention may rarely be used for an actual life-threatening event, the simplicity of design and implementation allows it to be employed in large populations of patients at modest risk with modest cost by non-cardiac electrophysiologists. Consequently, the US-ICD of the present invention focuses mostly on the detection and therapy of the most malignant rhythm disorders. As part of the detection algorithm's applicability to varying patient populations, the detection rate range is programmable upward or downward to meet the needs of the particular patient based on their cardiac condition and age.

Figure 2:
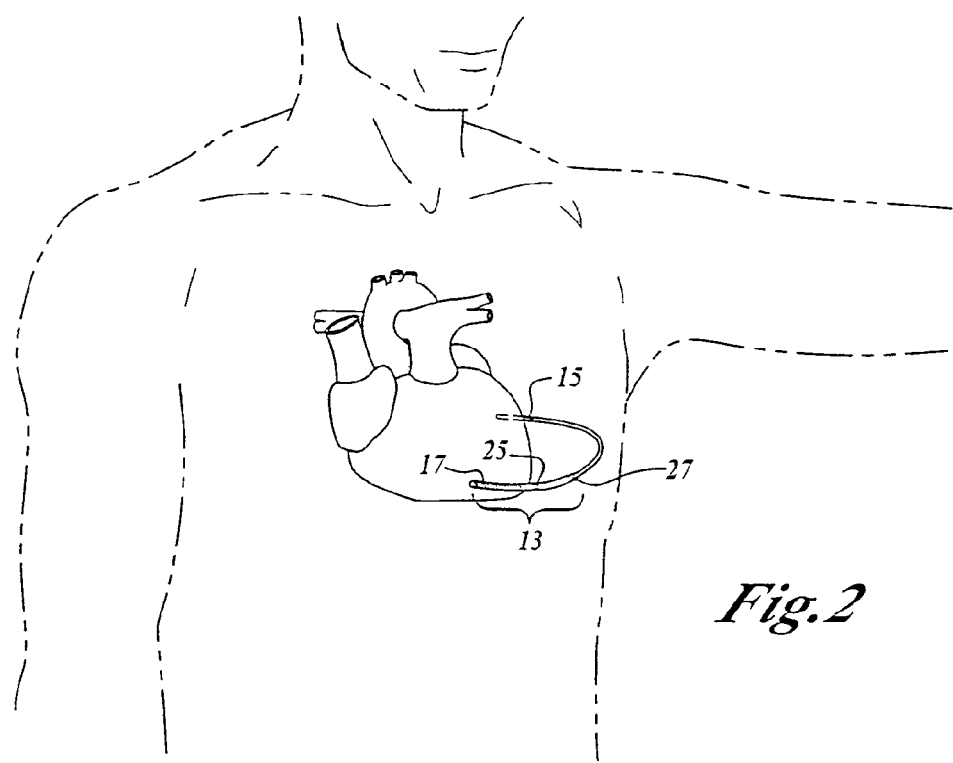
FIG. 2 is a schematic view of the US-ICD subcutaneously implanted in the thorax of a patient.

Turning now to FIG. 2, the optimal subcutaneous placement of the US-ICD of the present invention is illustrated. As would be evident to a person skilled in the art, the actual location of the US-ICD is in a subcutaneous space that is developed during the implantation process. The heart is not exposed during this process and the heart is schematically illustrated in the figures only for help in understanding where the device and its various electrodes are three-dimensionally located in the thorax of the patient. The US-ICD is located between the left mid-clavicular line approximately at the level of the inframammary crease at approximately the $5^{th}$ rib and the posterior axillary line, ideally just lateral to the left scapula. This way the US-ICD provides a reasonably good pathway for current delivery to the majority of the ventricular myocardium.

Figure 3:
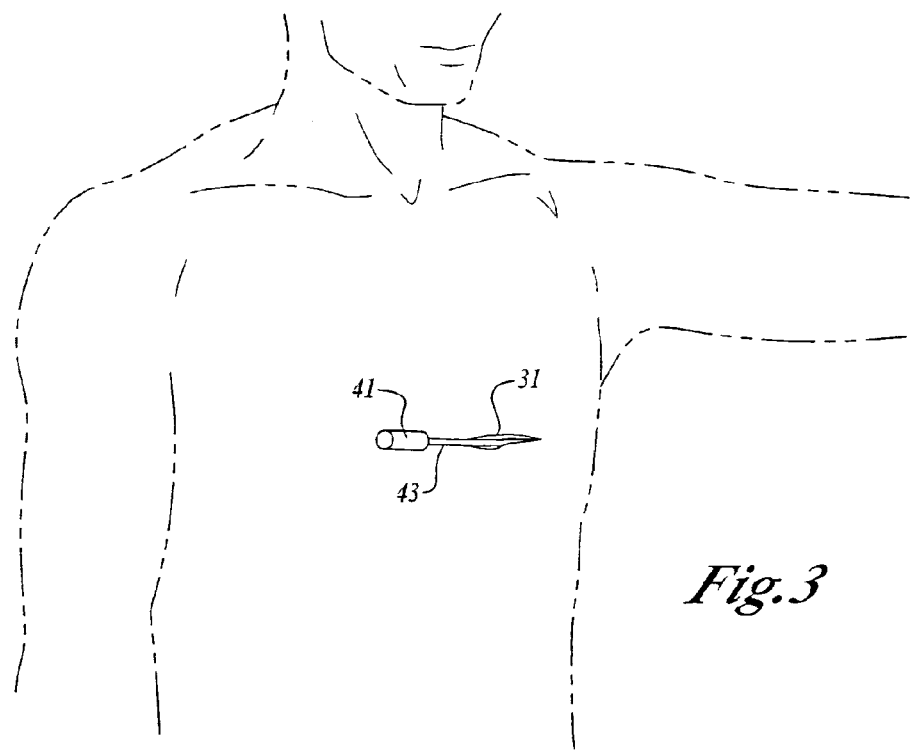
FIG. 3 is a schematic view of the method of making a subcutaneous path from the preferred incision for implanting the US-ICD.
Figure 4:
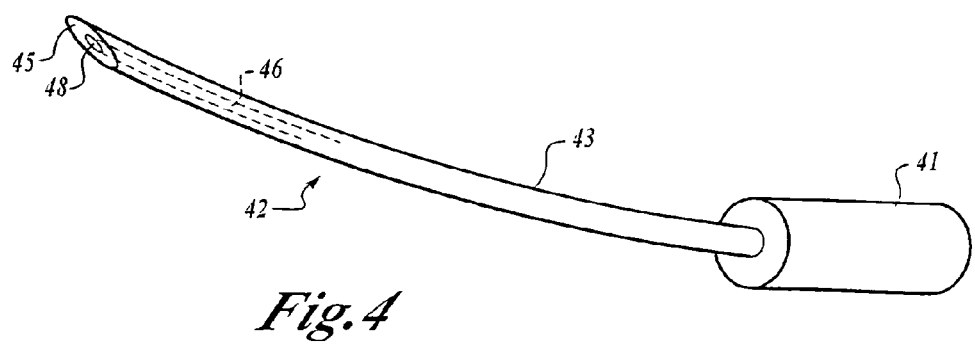
FIG. 4 is a schematic view of an introducer for performing the method of US-ICD implantation.

FIG. 3 schematically illustrates the method for implanting the US-ICD of the present invention. An incision 31 is made in the left anterior axillary line approximately at the level of the cardiac apex. A subcutaneous pathway is then created that extends posteriorly to allow placement of the US-ICD. The incision can be anywhere on the thorax deemed reasonable by the implanting physician although in the preferred embodiment, the US-ICD of the present invention will be applied in this region. The subcutaneous pathway is created medially to the inframammary crease and extends posteriorly to the left posterior axillary line. The pathway is developed with a specially designed curved introducer 42 (see FIG. 4). The trocar has a proximal handle 41 and a curved shaft 43. The distal end 45 of the trocar is tapered to allow for dissection of a subcutaneous pathway in the patient. Preferably, the trocar is cannulated having a central lumen 46 and terminating in an opening 48 at the distal end. Local anesthetic such as lidocaine can be delivered, if necessary, through the lumen or through a curved and elongated needle designed to anesthetize the path to be used for trocar insertion should general anesthesia not be employed. Once the subcutaneous pathway is developed, the US-ICD is implanted in the subcutaneous space, and the skin incision is closed using standard techniques.

Figure 5:
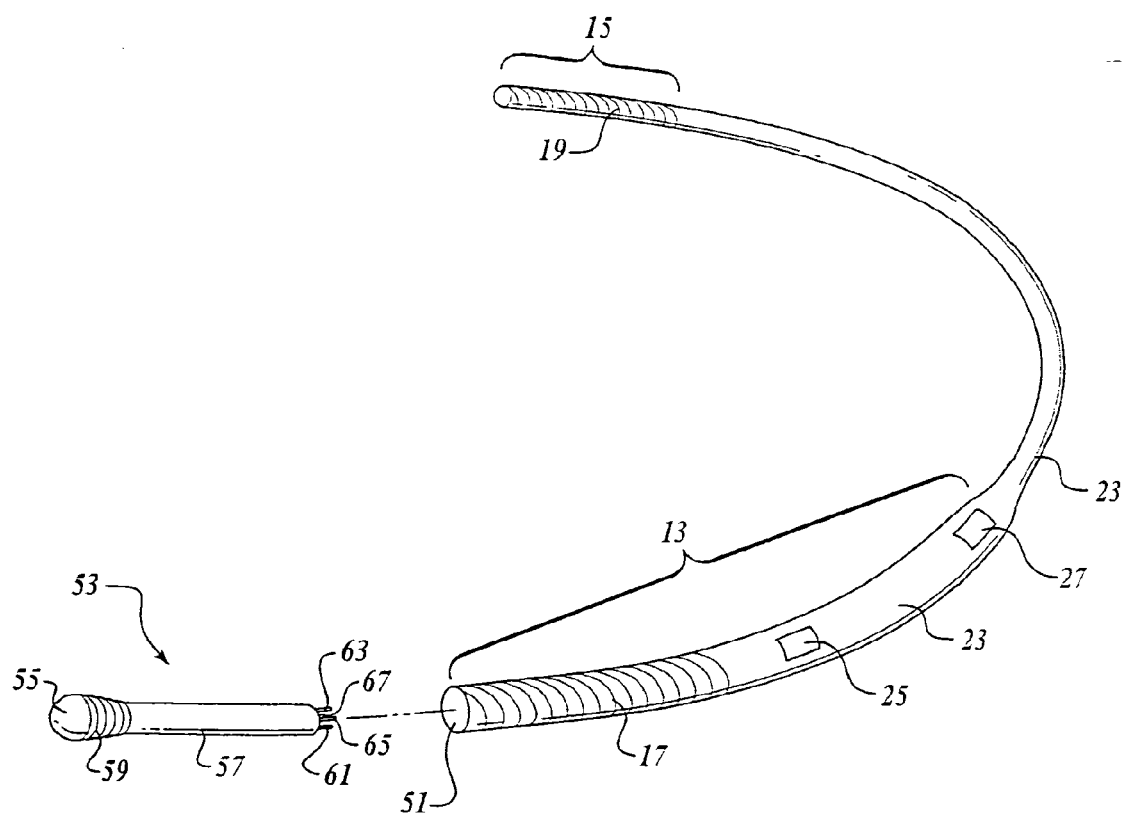
FIG. 5 is an exploded schematic view of an alternate embodiment of the present invention with a plug-in portion that contains operational circuitry and means for generating cardioversion/defibrillation shock waves.

As described previously, the US-ICDs of the present invention vary in length and curvature. The US-ICDs are provided in incremental sizes for subcutaneous implantation in different sized patients. Turning now to FIG. 5, a different embodiment is schematically illustrated in exploded view which provides different sized US-ICDs that are easier to manufacture. The different sized US-ICDs will all have the same sized and shaped thick end 13. The thick end is hollow inside allowing for the insertion of a core operational member 53. The core member comprises a housing 57 which contains the battery supply, capacitor and operational circuitry for the US-ICD. The proximal end of the core member has a plurality of electronic plug connectors. Plug connectors 61 and 63 are electronically connected to the sense electrodes via pressure fit connectors (not illustrated) inside the thick end which are standard in the art. Plug connectors 65 and 67 are also electronically connected to the cardioverter/defibrillator electrodes via pressure fit connectors inside the thick end. The distal end of the core member comprises an end cap 55, and a ribbed fitting 59 which creates a water-tight seal when the core member is inserted into opening 51 of the thick end of the US-ICD.

The core member of the different sized and shaped US-ICD will all be the same size and shape. That way, during an implantation procedure, multiple sized US-ICDs can be available for implantation, each one without a core member. Once the implantation procedure is being performed, then the correct sized US-ICD can be selected and the core member can be inserted into the US-ICD and then programmed as described above. Another advantage of this configuration is when the battery within the core member needs replacing it can be done without removing the entire US-ICD.

The US-ICD device and method of the present invention may be embodied in other specific forms without departing from the teachings or essential characteristics of the invention. The described embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

The invention claimed is:

1. A method of implanting a cardiac stimulus device into a patient comprising:
    developing a space for receiving the cardiac stimulus device beneath the skin and over the ribcage of the patient; and
    inserting a unitary cardiac stimulus device into the developed space;
    wherein:
    the unitary cardiac stimulus device comprises power supply, electronics, and electrodes such that, once implantation is complete, each of the power supply, electronics and electrodes are disposed within the developed space between the skin and the ribcage of the patient;
    the unitary cardiac stimulus device comprises an elongated housing that has an elongated shape that conforms to the shape of one of the patient's ribs once implanted;
    the unitary cardiac stimulus device lacks any transvenous leads;
    all of the electrodes of the unitary cardiac stimulus device are disposed on the housing, such that the implantation is completed without inserting any transvenous leads into the patient; and
    the step of inserting the unitary cardiac stimulus device into the developed space does not include accessing the patient's venous system.

2. The method of claim 1 wherein the developed space extends between the posterior axillary line and the anterior mid-clavicular line of the patient.

3. The method of claim 1 wherein the elongated housing has an elongated curve, the elongated curve of the housing sized to extend from an anterior region to a posterior region of the patient when implanted into the developed space.

4. The method of claim 1 wherein the unitary cardiac stimulus device comprises an outer housing that contains and protects the electronics, wherein the electrodes are disposed on the housing such that, once implanted in the developed space, at least a first electrode is disposed in a posterior region of the patient and a second electrode is disposed in an anterior region of the patient, with a portion of the patient's heart disposed therebetween.

5. The method of claim 1 wherein the unitary cardiac stimulus device includes at least three electrodes placed at spaced locations thereon; and the method further comprises programming the unitary cardiac stimulus device, once implanted, to use two best sensing electrodes in analyzing cardiac activity; and adapting the selection of two best sensing electrodes to changes in patient physiology over time.

6. The method of claim 5 wherein the unitary cardiac stimulus device comprises a canister having the electrodes thereon, the canister further comprising physical switches disposed thereon, and the step of programming the unitary cardiac stimulus device is done via the switches on the canister.

7. The method of claim 5 wherein the step of programming the unitary cardiac stimulus device is performed using a programming wand.

8. The method of claim 5 wherein the step of programming the unitary cardiac stimulus device is performed via a wireless connection.

9. The method of claim 5 wherein the space for implanting extends between the anterior mid-clavicular line and the posterior axillary line; and the step of inserting the unitary cardiac stimulus device is performed such that a first electrode is disposed near an end of the unitary cardiac stimulus device in a posterior region of the patient; second and third electrodes are disposed in an anterior region of the patient; and a fourth electrode is disposed near an end of the unitary cardiac stimulus device in an anterior region of the patient.

10. The method of claim 9 wherein the first and fourth electrodes are coupled to internal circuitry within the unitary cardiac stimulus device as defibrillation electrodes, and the second and third electrodes are coupled to the internal circuitry as sensing electrodes.

11. The method of claim 9 wherein the first and fourth electrodes are coupled to internal circuitry within the subcutaneous cardiac stimulus device as sensing electrodes, and the second and third electrodes are coupled to the internal circuitry as defibrillation electrodes.

12. The method of claim 5 wherein the unitary cardiac stimulus device has an elongated shape and generally conforms to one of the patient's ribs once implanted into the patient.

* * * * *